United States Patent [19]
Chatterjee

[11] Patent Number: 5,302,935
[45] Date of Patent: Apr. 12, 1994

[54] RENEWABLE GAS SENSOR, RENEWABLE GAS SENSOR BASE AND METHOD FOR RENEWING A GAS SENSOR

[75] Inventor: Dilip K. Chatterjee, Rochester, N.Y.
[73] Assignee: Eastman Kodak Company, Rochester, N.Y.
[21] Appl. No.: 987,931
[22] Filed: Dec. 8, 1992
[51] Int. Cl.⁵ .............................................. H01C 7/00
[52] U.S. Cl. ..................................... 338/34; 73/25.05; 73/31.05
[58] Field of Search ............... 338/34, 35; 73/23.2, 73/23.31, 25.01, 25.05, 30.04, 31.05, 31.06, 31.7; 204/402; 422/88, 90, 98

[56] References Cited

U.S. PATENT DOCUMENTS

| | | | |
|---|---|---|---|
| 4,197,089 | 4/1980 | Willis et al. | |
| 4,423,407 | 12/1983 | Zuckerman | 338/34 |
| 4,772,375 | 9/1988 | Wullschleger et al. | 204/402 |
| 4,822,456 | 4/1989 | Jones et al. | 204/192.1 |
| 4,950,378 | 8/1990 | Nagata | 204/402 |
| 5,057,436 | 10/1991 | Ball | 436/113 |
| 5,162,077 | 11/1992 | Bryan et al. | 204/402 |

*Primary Examiner*—Marvin M. Lateef
*Attorney, Agent, or Firm*—Clyde E. Bailey

[57] ABSTRACT

A renewable gas sensor, renewable gas sensor base and a method for renewing a gas sensor. The renewable gas sensor has a substantially planar heater. A substantially planar separator is superimposed on the heater. The separator is electrically insulating and thermally conducting. An electrode array is superimposed on the separator. The electrode array and the separator define a plurality of juxtaposed sensing sites disposed in electrically conductive relation to the electrode array and in thermally conductive relation to the separator. A chemical sensing film is superimposed on the separator and said electrode array in one of the sensing sites.

20 Claims, 2 Drawing Sheets

RENEWABLE GAS SENSOR, RENEWABLE GAS SENSOR BASE AND METHOD FOR RENEWING A GAS SENSOR

FIELD OF THE INVENTION

This invention relates to gas sensing and particularly relates to a renewable gas sensor, a gas sensor base and a method for renewing a gas sensor.

BACKGROUND OF THE INVENTION

A chemiresistor sensing device generally contemplates the use of a power supply transmitting current through a sensor which contains a semiconductor material, such as a metal oxide. The semiconductor material behaves as a chemiresistor. A chemical influence can be caused by an ambient gas interacting with the semiconductor material and can be monitored by a change in the resistance or conductance of the material by the use of electrodes which transmit the change in conductance to a monitor or detector, such as a voltmeter or ohmmeter.

A typical chemiresistor sensor has a resistor layer, such as a heater resistor, an electrical connection to the heater, a support layer, such as an alumina substrate, a conductor layer (often composed of interdigitated electrodes) and a deposited chemical sensing layer, for example tungsten oxide is used in U.S. Pat. No. 4,822,465 to detect sulfide. The thickness and manner in which the metal oxide semiconductor material is applied to the sensor electrodes are of importance to the functioning of the sensor, because the depth and microstructure of the metal oxide layer can affect both the selectivity and sensitivity of the tungsten oxide layer to sensed gas. The term "sensed gas" is used herein to designate one or more gases which will cause a change in resistivity of a chemiresistor gas sensor.

Thin film chemiresistor gas sensors have good response times, but are relatively expensive to produce and are subject to relatively rapid failure when used in an aggressive environment in which the sensor material itself is subject to degradation. Thin film sensors using semiconductor materials comprised of oxides, such as $WO_{3-x}$, $SnO_{-x}$, $KNb_3O_{8-x}$ and $ZnO_{1-x}$, where x is from 0 to 0.5, have shown good sensitivity for detecting reducing gases, such as hydrogen, anhydrous ammonia, hydrazine, propane, butane, methyl alcohol, ethyl alcohol and hydrogen sulfide. Willis et al., U.S. Pat. No. 4,197,089, discloses an example of a thin film hydrogen sulfide gas sensor. U.S. patent application Ser. No. 677,729, filed Mar. 29, 1991, by Royster et al, U.S. patent application Ser. No. 934,920, filed Aug. 25, 1992, by Royster et al, and U.S. patent application Ser. No. 934,937, filed Aug. 25, 1991, by Marrese et al disclose the preparation of a sensor layer and a hydrogen sulfide gas sensor. Zuckerman, U.S. Pat. No. 4,423,407, describes a gas sensor which can use a thin film or a thick porous layer. Gas sensors having a porous sensor layer have the shortcoming of slower resistivity response times, but are resistant to degradation, because they are thicker than comparable thin films.

Chemiresistor sensors have a further shortcoming that many sensor materials are subject to saturation with sensed gas. Partial saturation may permit continued, but possibly degraded, use; however, irreversible saturation of the sensor material necessitates replacement of the entire gas sensor.

It would therefore be desirable to provide a chemiresistor sensor which can use a thin film, is relatively rugged and can be renewed without replacement of the entire gas sensor and a sensor base and a method for renewing a gas sensor.

SUMMARY OF THE INVENTION

In the broader aspects of the invention, there is provided a renewable gas sensor, which has a substantially planar heater. A substantially planar separator is superimposed on the heater. The separator is electrically insulating and thermally conducting. An electrode array is superimposed on the separator. The electrode array and the separator define a plurality of juxtaposed sensing sites disposed in electrically conductive relation to the electrode array and in thermally conductive relation to the separator. A chemical sensing film is superimposed on the separator and said electrode array in one of the sensing sites.

There is further provided a renewable gas sensor base comprising a substantially planar heater, a substantially planar separator superimposed on the heater, and an electrode array superimpose on the separator. The separator is electrically insulating and thermally conducting. The electrode array and separator define a plurality of juxtaposed sensing sites disposed in electrically conductive relation to the electrode array and in thermally conductive relation to the separator. At least one sensing site is capable of receiving a chemical sensing film in superimposition on the separator and the electrode array.

There is further provided a method for renewing a gas sensor having an expended chemical sensing film and an unoccupied sensing site, comprising depositing by a physical film deposition technique an unexpended chemical sensing film in the unoccupied sensing site.

It is an advantageous effect of some of the embodiments of the invention that a gas sensor can be renewed after a first chemical sensing film becomes unusable.

BRIEF DESCRIPTION OF THE DRAWINGS

The above mentioned and other features and objects of this invention and the manner of attaining them will become more apparent and the invention itself will be better understood by reference to the following description of an embodiment of the invention taken in conjunction with the accompanying drawings wherein.

DESCRIPTION OF PARTICULAR EMBODIMENTS

Figure 1:
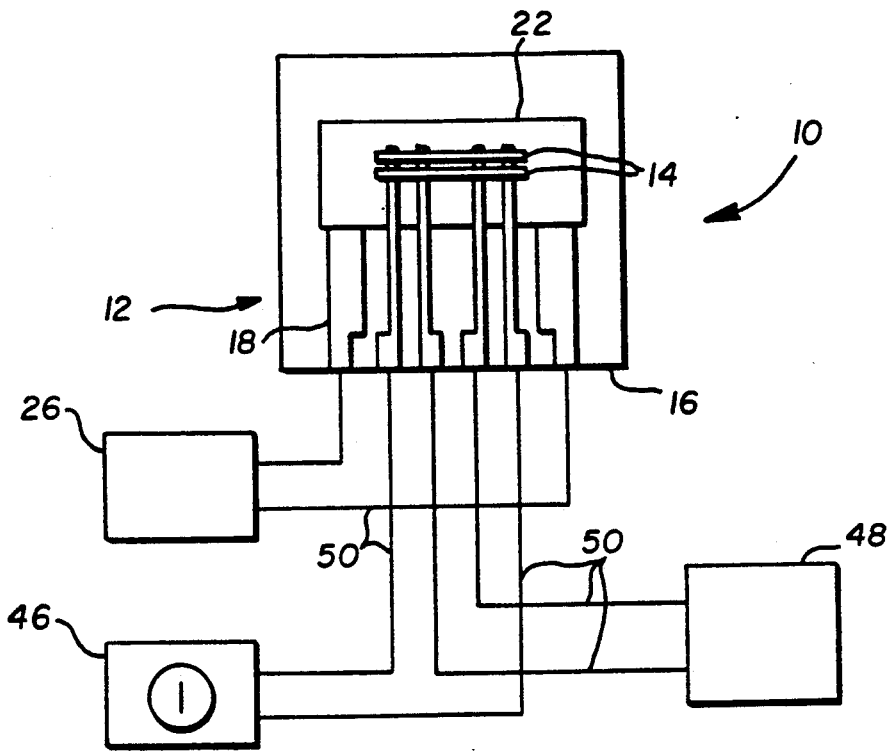
FIG. 1 is a schematic diagram which shows an embodiment of the renewable sensor of the invention incorporated in an electrical circuit.

Referring to the Figures, the renewable gas sensor 10 of the invention is an essentially planar, multilayer structure having a sensor base 12 and one or more chemical sensing films 14 overlaying sensor base 12. Sensor base 12 has five components 16,18,20,22,24, with a substrate 16 lowermost. Sensor elements 14,16,18,20,22,24, are depicted using hidden lines in FIG. 2 and separately in FIGS. 3–7. Components 18,20,22,24, are essentially planar layers overlaying substrate 16. It is desirable that each of components 18,20,22,24, of sensor base 12 have a thickness of greater than about 10 microns, since thicker layers resist erosion and other degradation during use in aggressive environments. Components 16,18,20,22,24, could, however, be thinner if desired. For example, components 16,18,20,22,24, could each have a thickness of about 1 micron.

Substrate 16 provides primary physical support and must consist of material which is capable of withstanding the environment conditions of preparation and use of renewable sensor 10, including renewal and reuse, without unacceptable degradation. Suitable materials for substrate 16 are well known to those skilled in the art, for example, aluminum oxide. A composite of different layers of material can be used if the uppermost layer of substrate 16 is electrically insulating. Other devices can be incorporated upon substrate 16 if those devices do not interfere with the preparation and use of sensor 10. Specific dimensions for substrate 16 are a matter of intended use and the limitations of manufacturing equipment. A convenient shape is that of a relatively thin wafer or plate.

Heater conductors 18 are deposited on substrate 16 and serve as an electrical path from an external heater electrical source 26. A suitable material for heater conductors 18 is an elemental metal or metal alloy, which is inert under the conditions encountered in preparation and use of sensor. For example, suitable materials for heater conductors 18 in an embodiment of renewable gas sensor 10 for detecting $H_2S$ and $SO_2$ are Au, Pt, Pt-Au, Cu, and Ni. For non-sulfur containing gases, Ag can be used as an electrode material. The larger two dimensions of heater conductors 18 are determined by the requirements of a particular use. In the embodiment shown in the Figures, heater conductors 18 have the shape of a pair of spaced apart pads which extend to the edge 28 of substrate 16.

Heater 20 is partially overlies and extends between heater conductors 18. Heater 20 is a resistor and acts to maintain renewable gas sensor 10 at a suitable operating temperature. A wide variety of materials could be used for heater 20, however, it is generally desirable to provide very accurate temperature control and many resistor materials would require use of an undesirably cumbersome external thermocouple. Preferred materials for heater 20, which do not require the use of a thermocouple, have positive or negative temperature coefficients of resistivity (PTCR and NTCR) and provide a substantially linear change in resistance with temperature. PTCR materials, such as barium titanate($BaTiO_3$), show nearly linear increases in resistance with temperature, whereas NTCR materials, such as manganese doped nickel oxide, show nearly linear decreases in resistance with temperature. The advantage of using a PTCR or NTCR material is that the temperature of heater 20 can be controlled very precisely, using a feedback circuit where any deviations of the resistance values of heater 20 can be compensated through input power. Example of such materials suitable for use in renewable gas sensor 10 are transition metal spinels, such as NiO and mixtures of such materials as $BaTiO_3$, $SrTiO_3$, and $PbTiO_3$. Resistance of heater 20 can be varied to meet particular needs by using different materials or by changing the geometry of heater 20.

Overlaying heater 20 is a separator 22, which is electrically insulating and thermally conducting. In the embodiment of the invention shown in the Figures, the two larger dimensions of separator 22 extend beyond heater 20 on all sides. Suitable materials for separator are materials having a dielectric constant above 4, including alumina ($Al_2O_3$) filled with glass, aluminosilicate, borosilicate, and soda-lime glasses An electrode array 24 overlays separator 22 and extends outward to edge 28 of substrate 16. Electrode array 24 defines a series of juxtaposed sensing sites 30, which each extend on the surface of separator 22 from one end 32 of electrode array 24 to the other end 34. Heater 20 underlies and extends beyond each sensing site 30 so as to provide uniform heating to all sensing sites 30.

Figure 2:
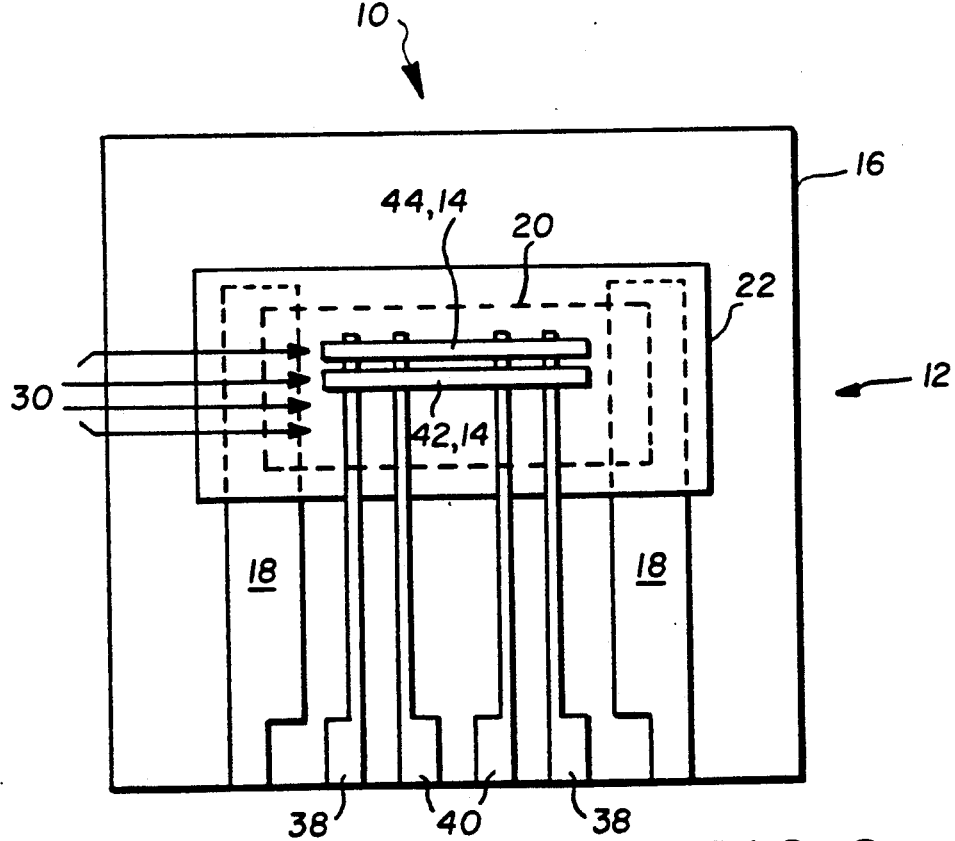
FIG. 2 is a surface view of the renewable sensor of FIG. 1. Dashed lines indicate the positions of hidden structures.
Figure 3:
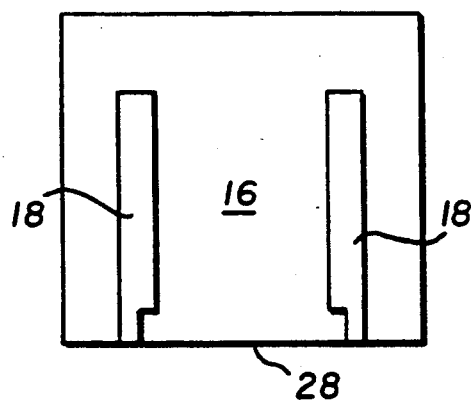
FIG. 3 is a top plan view of the substrate and heater electrodes of the renewable sensor of FIG. 1.
Figure 4:
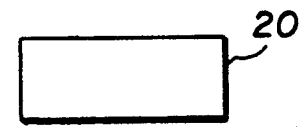
FIG. 4 is a top plan view of the heater of the renewable sensor of FIG. 1.
Figure 5:
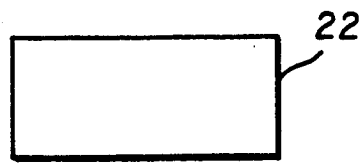
FIG. 5 is a top plan view of the separator of the renewable sensor of FIG. 1.
Figure 6:
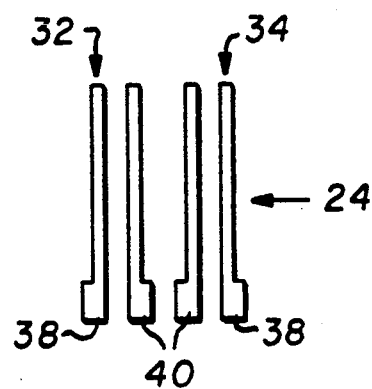
FIG. 6 is a top plan view of the electrode array of the renewable sensor of FIG. 1.
Figure 7:
FIG. 7 is a top plan view of an expended sensing film and a juxtaposed unexpended sensing film of the renewable sensor of FIG. 1.
Figure 8:
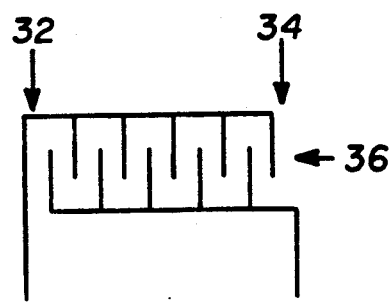
FIG. 8 is a top plan view of the conductor array of an alternative embodiment of the renewable sensor of the invention.

Electrode array 24 can consist of a single pair of spaced linear electrodes (not shown), or preferably, a pair of interdigitated electrodes 36 (shown in FIG. 8). It is more preferable, however, that a four probe array 24 be used as shown in FIGS. 1, 2, and 6. The four probe array 24 shown in the Figures has a pair of opposed outer or constant current electrodes 38, to the outside, and a pair of opposed inner or measuring electrodes 40, to the inside. The four probe electrodes 38,40 have the shape of parallel, spaced-apart strips with slightly enlarged pads at edge 28 of substrate 16. In the embodiments of the invention disclosed herein, sensing sites 30 extend transverse to electrodes of sensing array 24, where sensing sites 30 overlap electrodes.

The renewable sensor 10 of the invention has an unexpended chemical sensing film 42 disposed in one of the sensing sites 30 and may have one or more expended chemical sensing films 44 disposed in other sensing sites 30. The terms "expended" and "unexpended" are used herein in reference to chemical changes which occur in the material of the chemical sensing films 14 during use. These chemical changes, over time, destroy the utility of chemical sensing film 14 in sensor 10. These changes are irreversible without destruction or serious degradation of sensor 10. When a chemical sensing film 14 has chemically changed irreversibly such that the chemical sensing film 14 is no longer useful for chemical sensing, that chemical sensing film 14 is referred to herein as being "expended". Up until that time the chemical sensing film 14 is "unexpended".

Unexpended chemical sensing film 42 is a layer of semiconducting metal oxide suitable for detection of a particular gas. The use of particular metal oxides for particular gases is well known to those skilled in the art. Some suitable metal oxides are: $WO_{3-x}$, $SnO_{2-x}$, $KNb_3O_{8-x}$ and $ZnO_{1-x}$, where x is from 0 to 0.5. The semiconducting metal oxide can include a small percentage of a dopant. Examples of suitable dopants for H2S are silver, indium, gold and aluminum in amounts of 10 parts per million to 1 percent. Unexpended chemical sensing film 42 is a substantially uniform and continuous layer having a thickness of less than 1 micron.

Expended chemical sensing film 44 differs from unexpended chemical sensing film 42 chemically and may differ physically as well. Expended chemical sensing film 44 may be eroded or otherwise degraded so as to no longer be a substantially uniform and continuous layer. Expended chemical sensing film 44 also has a very high resistivity in comparison to unexpended chemical sensing film 42. Specific chemical differences will depend upon materials. For example, an unexpended chemical sensing film 42 of $WO_3$ used for the detection of $H_2S$ will over time change to $WO_{2-x}$, where x is from 0 to 0.5. This chemical change will also be accompanied by a change in color, from yellow to black. Expended and unexpended chemical sensing film 42 on an individual sensor 10 can also differ, not just in chemical changes due to use, but also due to different starting materials. For example, a sensor 10 could have an unexpended chemical sensing film 42 of $SnO_{2-x}$ and an expended film of $WO_{2-x}$.

In use, the renewable gas sensor 10 of the invention includes or is incorporated in an electrical circuit capable of exhibiting a measurable response to the change in resistivity of unexpended chemical sensing film 42, such as a standard operational amplifier circuit, in which a increase or decrease in resistance would cause a decrease or increase in voltage in direct proportion to the concentration of the particular gas. The resistance of unexpended chemical sensing film 42 changes when a sensed gas is ambient. It is believed this change in resistance is a result of an exchange mechanism between ions of the gas and the metal oxide, particularly the oxygen of the metal oxide. The very high resistance of any expended chemical sensing film 44 on sensor 10 does not change in the presence of the sensed gas. The expended chemical sensing film 44 is electrically in parallel with the much lower resistance of unexpended chemical sensing film 42 and has a negligible effect on sensor operation.

Referring now to FIG. 2, in embodiments of renewable gas sensor 10 having a four probe electrode array 24, constant current electrodes 38 are joined to a constant current supply 46 and measuring electrodes 40 are joined to a current responsive circuit element 48, such as a galvanometer. Circuit conductors 50 provide required electrical connections. A constant current is passed through unexpended chemical sensing film 42 and changes in resistance (conductance) are reflected as changes in current detected by detection element 48. Circuit element 48 can include recording means and the like in the same manner as well known sensor circuits. The advantage of four-probe embodiment of sensor 10 is that chemical and physical changes in the conductors and changes in resistances due to interaction with corrosive gases will not be reflected in the values of conductivity changes due to gas adsorption on the unexpended chemical sensing layer 42.

In an alternative embodiment of the invention having interdigitated electrodes 36, an average reading between "digits" is provided, which is highly precise. In this embodiment of the invention, it is desirable that electrodes 36 be made from material with low resistivity such as Au, Pd, Cu, or Ni.

Sensor base 12 is conveniently prepared by use of chemical deposition processes, well known to those skilled in the art. In a particular embodiment of the invention shown in the Figures, substrate base 12 was produced by screen printing layers over substrate 16 using 200 to 325 mesh screens with standard 1.0 mil. stainless steel wire attached to the frame at a 45 degree angle. The emulsions on the screens were 10–25 microns thick. A 30 durometer squeegee was used. The snap off distance was 40 mils. The pressure was set at one turn on the micrometer and the squeegee speed was about 2 inches/second. Prints were allowed to level for about 5 minutes, dried at 120° C. for 15 minutes, and finally air fired at peak temperature of 800° to 850° C. for 10 minutes. Other thick film techniques such as doctor blading and tape casting could also be used. Thin film techniques could be used for the preparation of substrate base 12, but would not be preferred.

Unexpended chemical sensing film 42 can be applied by a variety of physical film deposition techniques such as rf-sputtering, chemical vapor deposition and electron-beam evaporation. The various physical film techniques are widely known and, for example, are taught by Rointan F. Bunshah, Deposition Technologies for Films and Coatings; Park Ridge, N.J., 1982. Curing methods are necessary with some techniques, but are unnecessary with reactive sputtering. Dopants can be applied in conventional physical vapor deposition techniques. Dopants are mixed with the target material before the deposition process.

The renewable gas sensor 10 of the invention is renewed, in the method of renewing a gas sensor of the invention, by depositing a new unexpended chemical sensing film 42 in an unoccupied sensing site 30 on a sensor 10 having one or more expended chemical sensing films 44. This process can be repeated until all sensing sites 30 have been used. A variety of physical vapor deposition techniques can be used, but sputtering, reactive sputtering, and evaporation techniques are preferred. The expended chemical sensing films 44 are not removed, but is instead retained in juxtaposition to the new, unexpended chemical sensing film 42 on sensor base 12. Since the thin expended chemical sensing film 44 on the used gas sensor 10 is not reused degradation or partial erosion of the expended chemical sensing film 44 is immaterial. Components of sensor 10 base 12 can themselves degrade and erode, however, components are utilized as thick films to minimize these effects.

While the invention has been described with particular reference to a preferred embodiment, it will be understood by those skilled in the art that various changes may be made and equivalents may be substituted for elements of the preferred embodiment without departing from the invention. In addition, many modifications may be made to adapt a particular situation and material to a teaching of the invention without departing from the central teachings of the present invention.

What is claimed is:

1. A renewable gas sensor comprising a substantially planar heater, a substantially planar separator superimposed on said heater, said separator being electrically insulating and thermally conducting, an electrode array superimposed on said separator, said electrode array and said separator defining a plurality of juxtaposed sensing sites disposed in electrically conductive relation to said electrode array and in thermally conductive relation to said separator, and a chemical sensing film superimposed on said separator and said electrode array in one of said sensing sites.

2. The renewable gas sensor of claim 1 further comprising an expended sensing film disposed in another said sensing site.

3. The renewable gas sensor of claim 1 wherein said heater underlies and extends beyond each said sensing site in directions parallel to the two largest dimensions of said sensing sites.

4. The renewable gas sensor of claim 1 wherein said heater layer is composed of a material selected from the group consisting of materials having a positive temperature coefficient of resistivity and materials having a negative temperature coefficient of resistivity.

5. The renewable gas sensor of claim 4 wherein said electrode array further comprises a pair of opposed constant current electrodes and a pair of opposed measuring electrodes, said measuring electrodes being disposed between said constant current electrodes.

6. The renewable gas sensor of claim 5 further comprising means for supplying a constant current to said constant current electrodes and a current responsive circuit element in electrically conducting contact with said measuring electrodes.

7. The renewable gas sensor of claim 6 wherein said heater, said separator, said electrode array, said heater electrodes and said substrate, each have a thickness greater than 10 microns and said chemical sensing film has a thickness of less than 1 micron.

8. The renewable gas sensor of claim 7 wherein said chemical sensing film is a semiconducting metal oxide selected from the group consisting of: doped and undoped; tungsten oxides, tin oxides, niobium oxides, and zinc oxides.

9. The renewable gas sensor of claim 8 wherein said chemical sensing film comprises $WO_{3-x}$, wherein x is from 0 to 0.5.

10. The renewable gas sensor of claim 1 wherein said electrode array further comprises a pair of opposed constant current electrodes and a pair of opposed measuring electrodes, said measuring electrodes being disposed between said constant current electrodes.

11. The renewable gas sensor of claim 10 further comprising means for supplying a constant current to said constant current electrodes and a current responsive circuit element in electrically conducting contact with said measuring electrodes.

12. The renewable gas sensor of claim 1 wherein said electrode array extends substantially transverse to said sensing sites.

13. The renewable gas sensor of claim 1 wherein said chemical sensing film has a thickness of less than 1 micron.

14. The renewable gas sensor of claim 1 wherein said heater, said separator, and said electrode array, each have a thickness of greater than 10 microns.

15. The renewable gas sensor of claim 1 wherein said heater, said separator, said electrode array, said heater electrodes and said substrate, each have a thickness greater than 10 microns and said chemical sensing layer has a thickness of less than 1 micron.

16. The renewable gas sensor of claim 1 wherein said chemical sensing film is a semiconducting metal oxide selected from the group consisting of: doped and undoped; tungsten oxides, tin oxides, niobium oxides, and zinc oxides.

17. A renewable gas sensor base comprising a substantially planar heater, a substantially planar separator superimposed on said heater, said separator being electrically insulating and thermally conducting, an electrode array superimposed on said separator, said electrode array and said separator defining a plurality of juxtaposed sensing sites disposed in electrically conductive relation to said electrode array and in thermally conductive relation to said separator, at least one said sensing site being capable of receiving a chemical sensing film in superimposition on said separator and said electrode array.

18. The renewable gas sensor base of claim 17 wherein said heater, separator, and electrode array, each have a thickness greater than 10 microns.

19. A method for renewing a gas sensor having an expended chemical sensing film and an unoccupied sensing site, comprising depositing by a physical film deposition technique an unexpended chemical sensing film in said unoccupied sensing site.

20. The method of claim 19 wherein said unexpended chemical sensing film has a thickness of less than 1 micron.

* * * * *